US 11,989,831 B1

United States Patent
Jain et al.

(10) Patent No.: US 11,989,831 B1
(45) Date of Patent: May 21, 2024

(54) USER-INTERFACE FOR VISUALIZING ELECTRO-ANATOMICAL DATA WITH SELECTIVE CONTROL FOR EXPOSING METRICS

(71) Applicant: Neucures Inc., Los Angeles, CA (US)

(72) Inventors: Rohit Jain, Danville, CA (US); Padmaja Narsipur, Bangalore (IN)

(73) Assignee: NEUTRACE INC., Longwood, FL (US)

( * ) Notice: Subject to any disclaimer, the term of this patent is extended or adjusted under 35 U.S.C. 154(b) by 0 days.

(21) Appl. No.: 16/952,298

(22) Filed: Nov. 19, 2020

(51) Int. Cl.
*G06T 17/20* (2006.01)
*G06T 19/20* (2011.01)

(52) U.S. Cl.
CPC .............. *G06T 17/20* (2013.01); *G06T 19/20* (2013.01); *G06T 2200/24* (2013.01); *G06T 2219/2012* (2013.01)

(58) Field of Classification Search
CPC ..... G06T 17/20; G06T 19/20; G06T 2200/24; G06T 2219/2012
See application file for complete search history.

(56) References Cited

U.S. PATENT DOCUMENTS

| 9,351,657 | B2 * | 5/2016 | Govari | A61B 5/349 |
| 2006/0239548 | A1 * | 10/2006 | George Gallafent et al. | G06T 7/11 382/164 |
| 2008/0221425 | A1 * | 9/2008 | Olson | A61B 90/36 600/407 |
| 2008/0249395 | A1 * | 10/2008 | Shachar | A61B 34/76 600/409 |
| 2016/0061599 | A1 * | 3/2016 | Zeng | A61B 5/061 702/150 |
| 2016/0067007 | A1 * | 3/2016 | Piron | G16H 40/20 705/3 |

FOREIGN PATENT DOCUMENTS

JP 2015031539 A * 2/2015

* cited by examiner

*Primary Examiner* — Jeffery A Brier
(74) *Attorney, Agent, or Firm* — Caldwell Intellectual Property Law

(57) ABSTRACT

A method for a graphical user interface (GUI) of a computer system is provided. The method comprises displaying within a first portion the GUI, an electro-anatomical map of the heart, said electro-anatomical map comprising a plurality of measurement points within the heart for which data was collected; displaying a plurality of markers, each representing a respective one of said measurement points spatially in relation to the geometry of the heart within said first portion; determining, by a processor, user-selection of a particular measurement point within the heart through selection of its associated marker; responsive to said user-selection of the particular measurement point, retrieving at least one metric associated with said measurement point; and displaying in a second portion of the GUI, each retrieved metric associated with a particular measurement point within the heart.

3 Claims, 16 Drawing Sheets

USER-INTERFACE FOR VISUALIZING ELECTRO-ANATOMICAL DATA WITH SELECTIVE CONTROL FOR EXPOSING METRICS

FIELD

Embodiments of the present invention relate to systems and methods for electrophysiological cardiac mapping.

BACKGROUND

Cardiac mapping may be performed with catheters that are introduced percutaneously into the heart chambers and sequentially record the endocardial electrograms with the purpose of correlating local electrogram to cardiac anatomy.

Mapping systems may record data including catheter locations within the heart and intracardiac electrograms at each location. This data may be used to reconstruct in real-time a representation of the three-dimensional geometry of the chamber, color-coded with relevant electrophysiological information.

SUMMARY

Broadly, embodiments of the present invention disclose techniques for a graphical user interface (GUI) of a computer system, comprising:
displaying within a first portion the GUI, an electro-anatomical map of the heart, said electro-anatomical map comprising a plurality of measurement points within the heart for which data was collected;
displaying a plurality of markers, each representing a respective one of said measurement points spatially in relation to the geometry of the heart within said first portion;
determining, by a processor, user-selection of a particular measurement point within the heart through selection of its associated marker;
responsive to said user-selection of the particular measurement point, retrieving at least one metric associated with said measurement point; and
displaying in a second portion of the GUI, each retrieved metric associated with a particular measurement point within the heart.

Other aspects of the invention, will be apparent from the written description below.

DETAILED DESCRIPTION

In the following description, for purposes of explanation, numerous specific details are set forth in order to provide a thorough understanding of the invention.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not others.

Moreover, although the following description contains many specifics for the purposes of illustration, anyone skilled in the art will appreciate that many variations and/or alterations to said details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

As will be appreciated by one skilled in the art, the aspects of the present invention may be embodied as a system, method or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, aspects of the present invention may take the form of a computer program product embodied in one or more computer readable medium(s) having computer readable program code embodied thereon.

Figure 1:
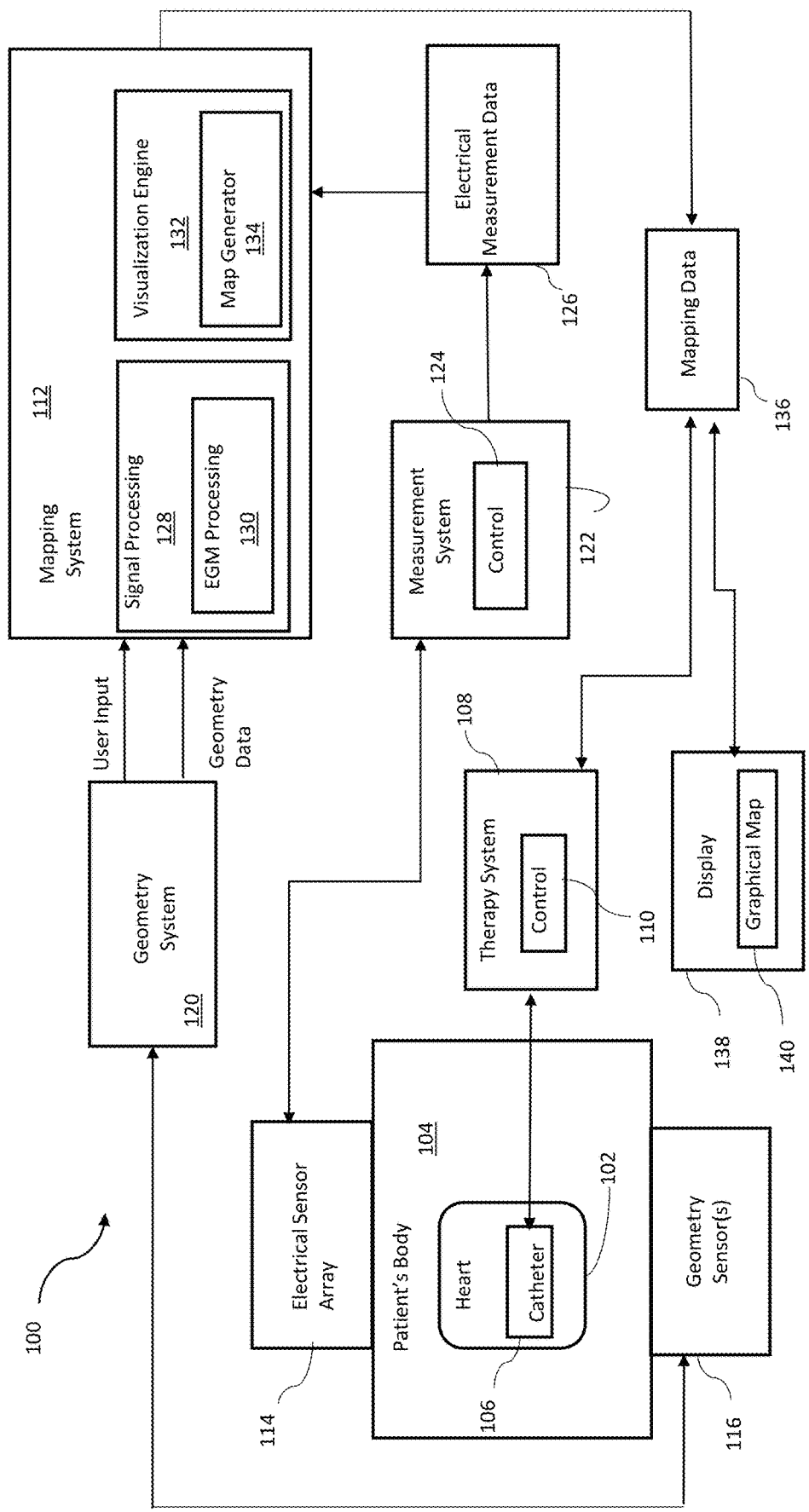
FIG. 1 of the drawings shows an exemplary diagnostic/treatment system, in accordance with one embodiment of the invention.

FIG. 1 of the drawings shows an exemplary diagnostic/treatment system 100, in accordance with one embodiment of the invention. The system 100 is capable of assessing the condition of the heart 102 in real-time as part of a treatment or diagnostic procedure. For this purpose, the system 100 includes one or more catheters that can be inserted into a patient's body 104 thereby to contact the patient's heart 102—more specifically the endocardium or the epicardium. One of ordinary skill in the art would understand and appreciate that various types and configurations of therapy delivery device 106 may be utilized, depending on the type of treatment and procedure.

In some cases, the therapy delivery device 106 may include an ablation catheter one or more electrodes located at its tip which in use is configured to ablate tissue in response to electrical signals, for example using radiofrequency energy supplied by a therapy system 108. In other cases, the therapy delivery device 106 may include one or more electrodes located at the tip of a pacing catheter to deliver electrical stimulation for pacing the heart in response The therapy system 108 may be located external to the patient's body 104 and may be configured to control the type of therapy that is delivered by the therapy delivery device 106. For example, the therapy system 108 may include control circuitry 110 configured to deliver electrical signals by a conductive link electrically connected between the device (electrodes) 106 and the therapy system 108. The control circuitry 110 may provide control parameters for the signals supplied to the device 106 (these may include current, voltage, etc.) For delivering therapy (example ablation) via the electrode (s) 106 to one or more sites within the heart 102, the control circuitry 110 may set therapy parameters and apply stimulation based on automatic, manual (user input) or a combination of automatic and manual mechanisms. In some embodiments, one or more sensors (not shown) may be configured to communicate since the information back to the therapy system 108. The position of the catheter 106 within the heart 102 may be determined and tracked by a mapping system 112. Location of the device 106 and the therapy parameters may be combined to provide corresponding therapy parameter data.

In some embodiments, prior to providing therapy by the therapy system 108 another system or subsystem may be utilized to acquire electrophysiological data for the patient. For this purpose, a sensor array 114 including one or more electrodes may be utilized for recording patient activity. In some cases, the sensor array 114 may include an arrangement of body surface sensors distributed over a portion of the patient's torso for measuring electrical activity associated with the patient's heart. The catheter 106 may include one or more electrodes that can be utilized in conjunction with the sensor array 114 for mapping electrical activity of the endocardial surface such as the wall of the heart chamber. Additionally, such electrodes may be used to obtain location or positional information of the catheter 106 within the heart which can advantageously be used to register electrical information of the heart in an image or map generated by the system 100. In some embodiments, to facilitate the tracking of the catheter 106 positional within the heart, geometry sensors 116 may be positioned around the patient's body and configured to sense the position of the catheter 106 within the heart. For example, in some embodiments, the catheter 106 may be comprise a magnetic element that can be sensed by the geometry sensors 116 to derive catheter positional data that is transmitted to a geometry system 120. The geometry system 120 may be configured to generate geometry data which is then input into the mapping systems 112.

In one embodiment, the sensor array 114 may be configured to provide the sensed electrical information to a corresponding measurement system 122. The measurement system 122 may include control circuitry 124 and signal processing circuitry (not shown) for generating electrical measurement data 126 that describes electrical activity detected by sensors in the sensor array 114. The electrical measurement data 126 may comprise analog and/or digital information. In some embodiments, the control circuitry 124 may be configured to control a data acquisition process for measuring electrical activity of the heart and generating the electrical measurement data 126. The electrical measurement data 126 may be acquired concurrently with the therapy delivered by the therapy system 108.

The mapping system 112 may be configured to combine the electrical measurement data 126 with geometry data generated by the geometry system 120 by applying appropriate processing computations. For example, the mapping system 112 may include a single processing module 128 configured to process the signals generated by the geometry system 120 and the measurement system 122. For example, the signal processing module 128 may include an EGM processing module 130 configured to process EGM signals associated with the heart. A visualize relation engine 132 of the mapping system 112 may be provisioned with a map generator function 134 configured to render various metrics associated with the heart in visual form. For this purpose, the visualization engine 132 outputs mapping data 136 that can be rendered on a display 138 as a graphical map 140 showing various metrics associated with the heart.

By way of example, the geometry data output by the geometry system 120 may comprise a graphical representation of the patient's heart in the form of image data acquired for the patient. In one embodiment, the geometry system 120 may process the image data to extract and segment anatomical features of the heart. Additionally, positional information for the sensors within the electrical sensor array 114 may be included in the geometry data. The geometry data may be converted into a two-dimensional or three-dimensional graphical representation that includes regions of interest within the patient's heart by the mapping system 112.

In other embodiments, the geometry data may include a mathematical model of the patient's heart instructed based on image data for the patient. Anatomical or other landmarks, including locations for the electrodes within the sensor array 114 may be identified in the geometry data to facilitate registration of the electrical measurement data 126. Identification of said landmarks may be performed manually based on the user input, or automatically by means of image processing techniques.

The map generator 134 may be configured to generate activation maps for the patient's heart, showing various metrics such as electrical activation times, and indications for QRS onset, the DV/DT, fractionation, etc.

Figure 2:
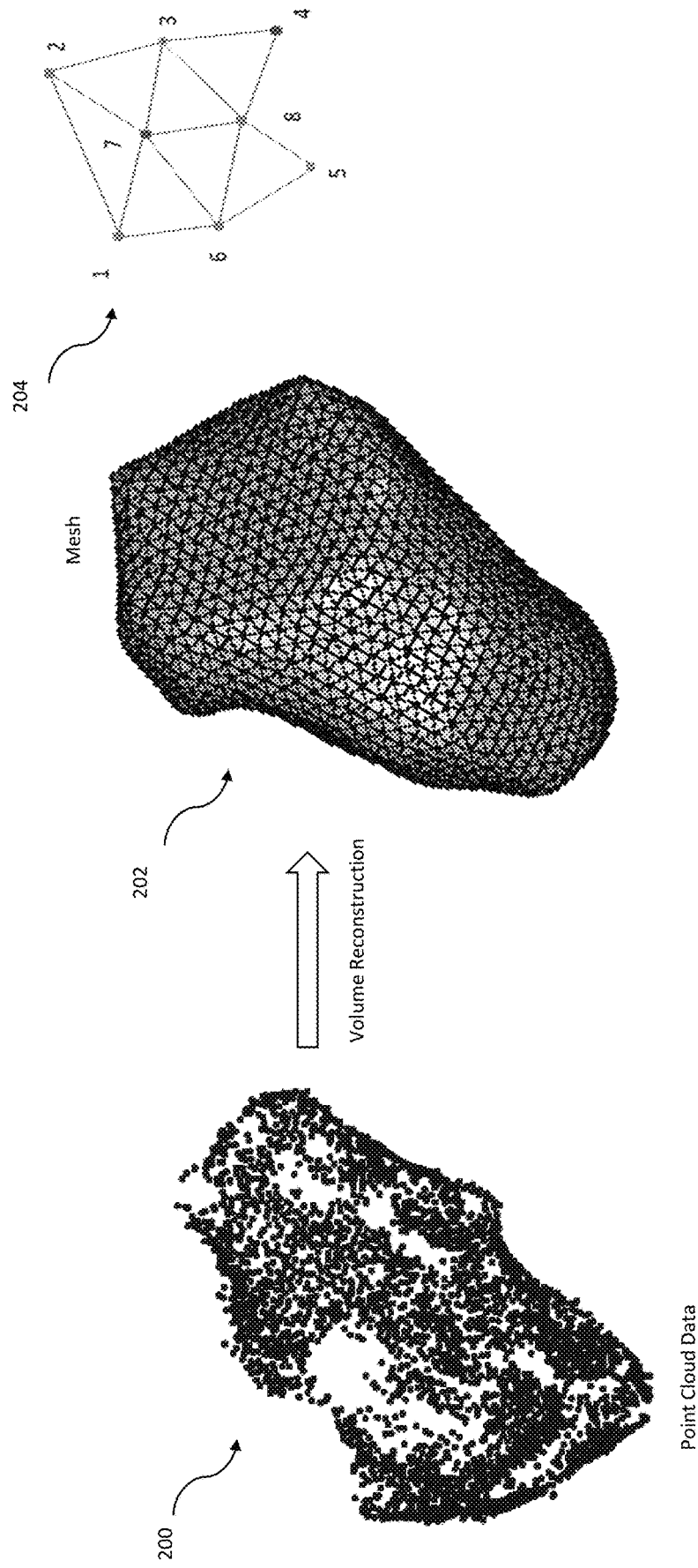
FIG. 2 illustrates a process for generating a mesh from point cloud data, in accordance with an embodiment of the invention.

Reference is now made to FIG. 2, which shows a point cloud 200 of cardiac data obtained from locations within the heart in accordance with an embodiment of the invention. Such a point cloud may be acquired by for locations reported by a location sensor on the catheter, as known in the art The point cloud data 200 may be associated with respective coordinates in a 3-dimensional space, based on anatomic landmarks or fiducial marks, using location information provided by geometry sensors 116 on a catheter 106.

Figure 3:
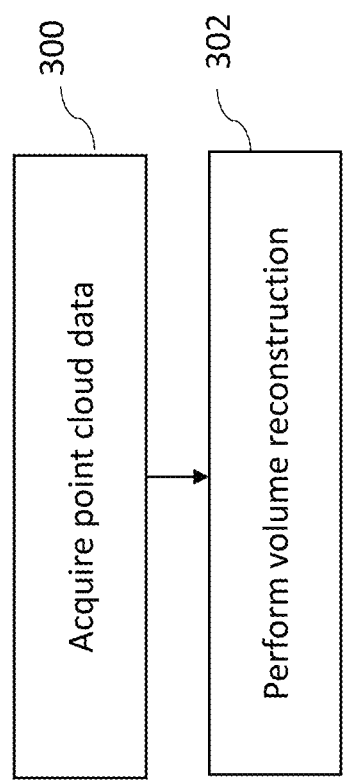
FIGS. 3 and 4 illustrate specific processing steps for generating a mesh from point cloud data, in accordance with an embodiment of the invention.

Reference is now made to FIG. 3, which is a flow chart of a method for 3-dimensional anatomical reconstruction from a point cloud, in accordance with an embodiment of the invention. At initial step 300, a point cloud of a structure, e.g., the point cloud 200 (FIG. 2) of a heart or portion thereof is acquired as described above, using the facilities of the system 100 (FIG. 1) or an equivalent system.

Next, at step 302 an initial volume reconstruction is prepared from the point cloud that was obtained in initial step 300. It should be noted that initial step 300 and step 302 may be performed in the same or different catheterization sessions. One way of performing step 302 is associating data 200 with the center of a corresponding volume element or voxel (not shown) and performing the process steps described below.

In one embodiment, during volume reconstruction the mapping system 112 initially connects locations of the point cloud 200, to define a mesh 202 (FIG. 2). In FIG. 2, reference numeral 204 generally indicates a portion of the mesh numeral 202 in greater detail. As will be seen, the mesh comprises the locations or data points (indicated by the numbers 1-8) at which data was collected.

After producing the mesh 202, a generally smooth surface connecting data points and line segments, to produce triangular interconnected regions. To generate the surface the interpolation and additionally or alternatively extrapolation may be used, in one embodiment.

In one embodiment, after generating the smooth surface, a check is performed to determine if the surface is closed, i.e., if the surface is topologically equivalent to a closed surface such as a sphere. If the surface is not closed, the mapping system 112 may close the surface by adding further surface elements until the surface is closed.

Figure 4:
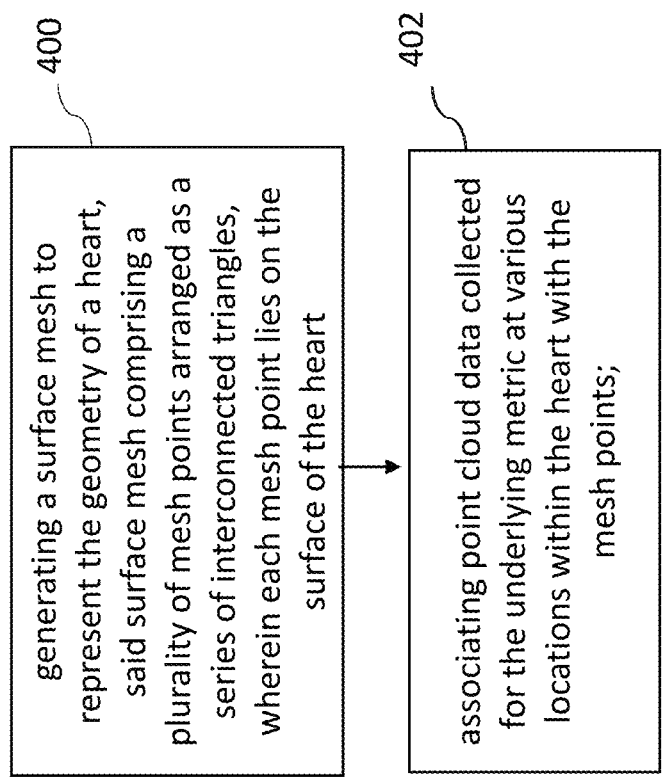

In accordance with one embodiment, the steps associated with the technique of volume reconstruction may include the steps 400 and 402 (FIG. 4) which includes generating a surface mesh to represent the geometry of the heart, said surface mesh comprising a plurality of mesh points arranged as a series of interconnected triangles, wherein each mesh point lies on the surface of the heart; and associating point cloud data in various locations within the heart with the mesh points, respectively. Advantageously in one embodiment, the point cloud data also includes underlying metrics collected at the various locations, as described below.

Once the mesh for the heart is determined based on the point cloud data, as described above, the mapping system 112 may output an electro-anatomical map on the display numeral 138. The electro-anatomical map may be configured to illustrate various metrics associated with the heart. Said metrics may include the QRS onset, fractionation, DV/DT min, and electrogram depolarization voltage as described in co-pending U.S. patent application Ser. No. 17/073,211 entitled "METHOD AND SYSTEM FOR DETERMINING QRS ONSET IN CARDIAC SIGNALS", U.S. Ser. No. 17/073,220 entitled "METHOD AND SYSTEM FOR MEASURING UNIPOLAR AND BIPOLAR CARDIAC ELECTROGRAM FRACTIONATION", U.S. Ser. No. 17/073,230 entitled "METHOD AND SYSTEM FOR MEASURING CARDIAC TISSUE HEALTH BASED ON DV/DT MIN OF A DEPOLARIZATION WAVE WITHIN THE CARDIAC ELECTROGRAM", U.S. Ser. No. 17/073,239 entitled "METHOD AND SYSTEM FOR MEASURING CARDIAC ELECTROGRAM DEPOLARIZATION VOLTAGE", each of which is incorporated by reference herein.

Figure 5:
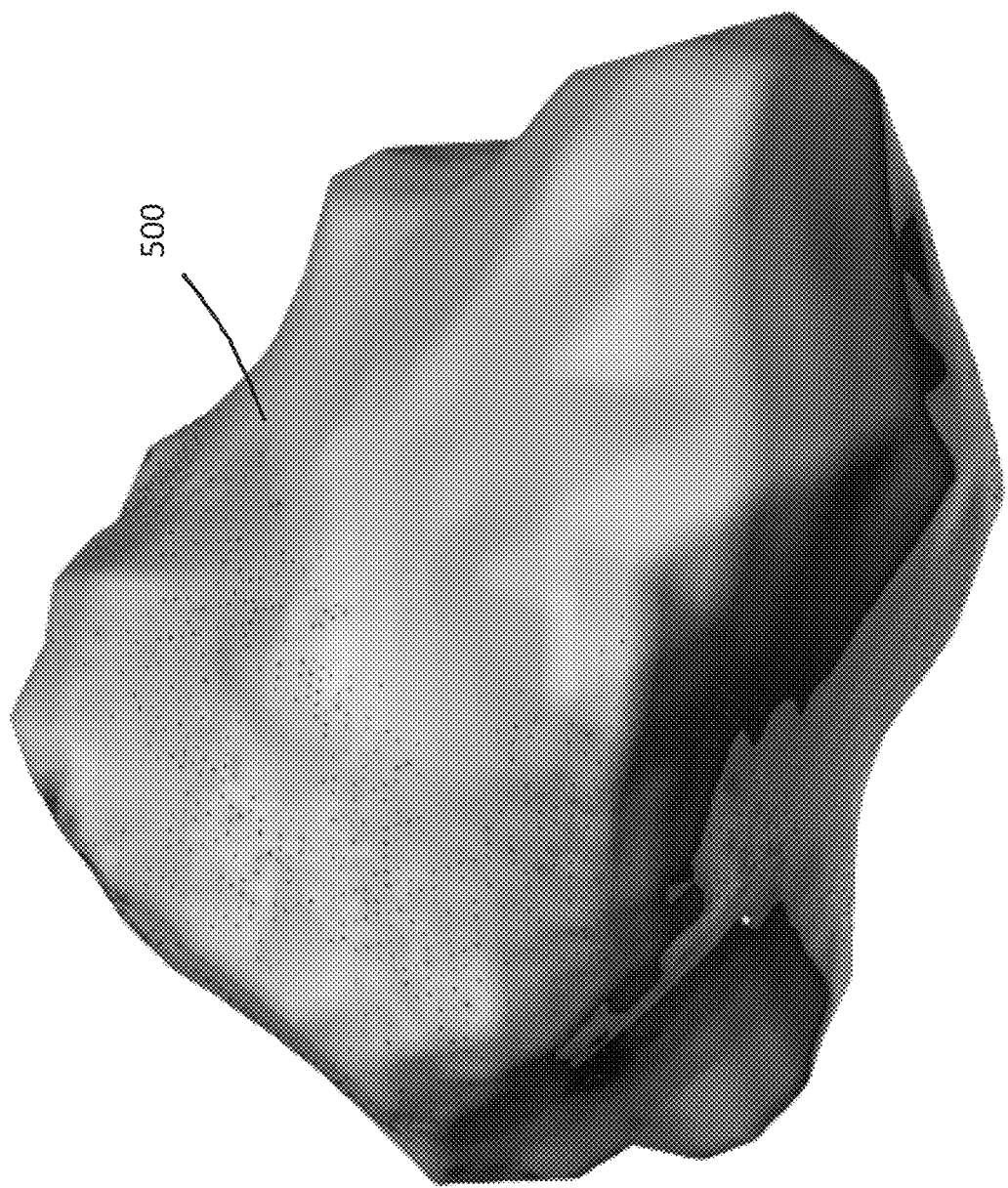
FIGS. 5, 9, and 11 of the drawings illustrate cardiac maps produced in accordance with one embodiment of the invention.

In one embodiment, the map generator 134 may output mapping data 136 to generate an electro-anatomical map 500 of the heart as shown in FIG. 5. As will be seen, the map 500 is colored in accordance with a color scale. The color scale is chosen so that the colors indicative of diseased and healthy cardiac tissue. Prior to the techniques of the present invention, choosing the color scale was somewhat arbitrary depending on the skill of an electrophysiologist and had no bearing on the actual data is to produce the map. This issue is solved by the present invention, according to the steps illustrated in FIG. 6 of the drawings.

Figure 6:
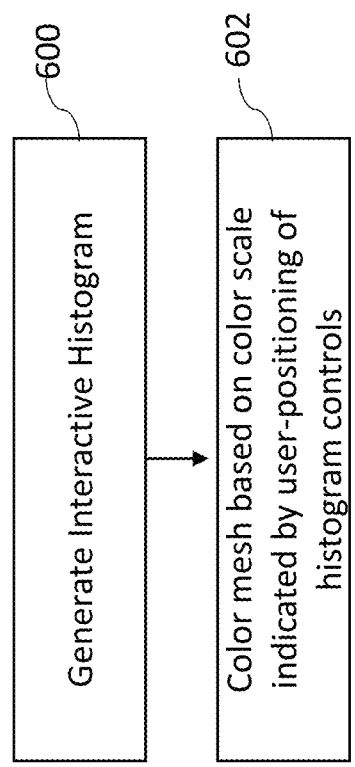
FIG. 6 illustrating a process steps for coloring a cardiac map, in accordance with one embodiment of the invention.
Figure 7:
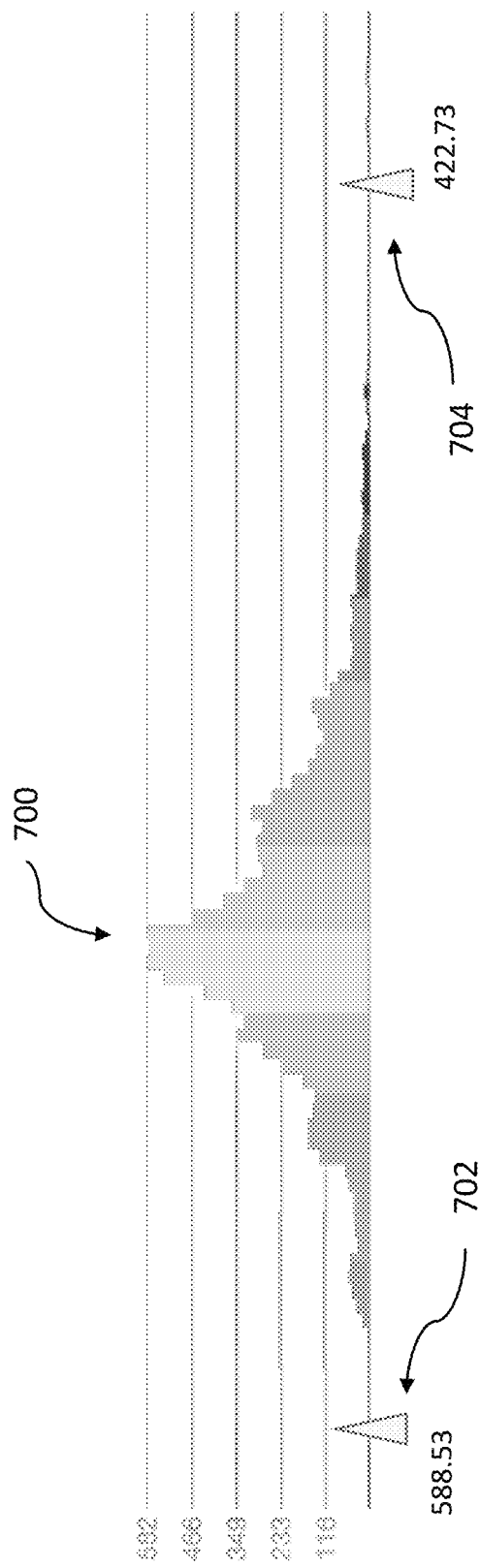
FIGS. 7, 8, and 10 illustrate aspects of an interactive histogram, in accordance with an embodiment of the invention.

Referring to FIG. 6, at block 600 and interactive histogram is generated and displayed on the display numeral 138. An example of the interactive histogram, in accordance with one embodiment, is indicated by reference numeral 700 in FIG. 7 of the drawings. The histogram 700 depicts values for an underlying metric, for example activation time, currently shown on the cardiac map currently being viewed. The Y-axis of the histogram shows the complete the range of values measured/computed for the underlying metric, whereas the Y-axis shows a number of points in the heart exhibiting a particular metric value. The histogram 700 is described as interactive because it comprises a left control 702 and a right control 704 that can be adjusted or slid to the left or right to set the outer boundaries of the values of the underlying metric to be used in the process of countering the heart. This process of setting the color range will now be described.

Looking at the histogram 700 in greater detail, it will be seen that the left control 702 is set to the value of 588.53, whereas the right to control numeral 704 is set to the value numeral 422.73. These values define the upper and lower limit for the color scale to be used in coloring the cardiac map. What this means is that the value of 588.53 is assigned to one color in the color scale, whereas the value numeral 422.73 is assigned to another color in the color scale; each of these colors defining extremities in the scale. By a process of interpolation, values between these extremities will be assigned a color. In the histogram 700, it will be seen that the control 702, and 704 are placed at a value where there is no data in the histogram, thus setting the color scale based on these positions would lead to a loss of resolution or detail in the cardiac map. Indeed, the map 500, was colored based on the settings of the histogram 700. As will be noted, a significant portion of the map 500 is colored green and shows an area that has very little underlying data. Thus, the map 500 colored based on the color scale indicated by the histogram 700 does not show an electrophysiologist much about the condition of the underlying heart tissue.

Figure 8:
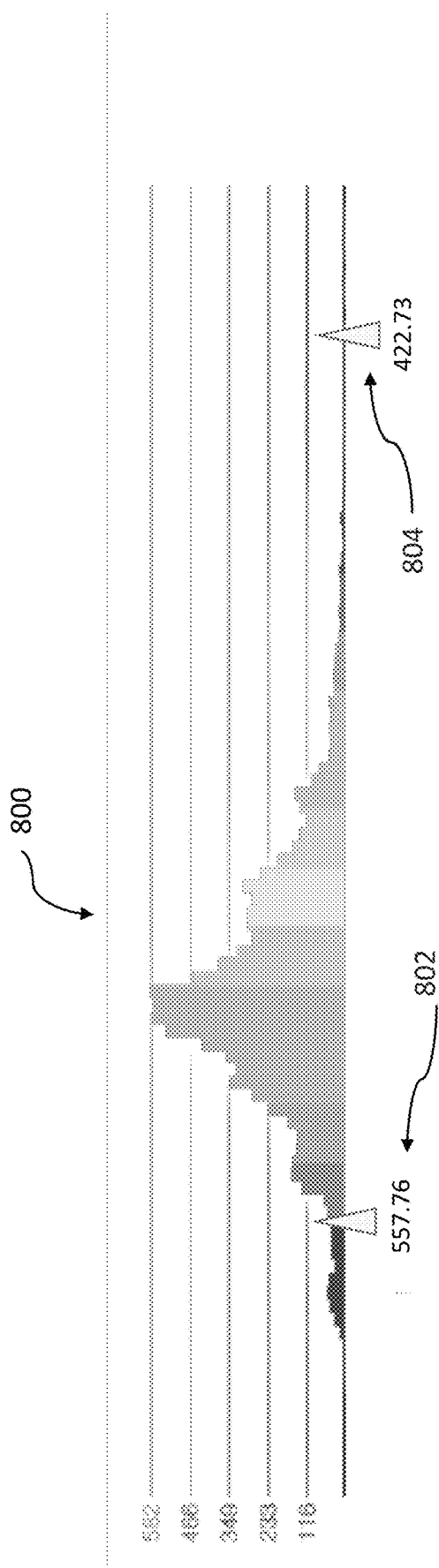
Figure 9:
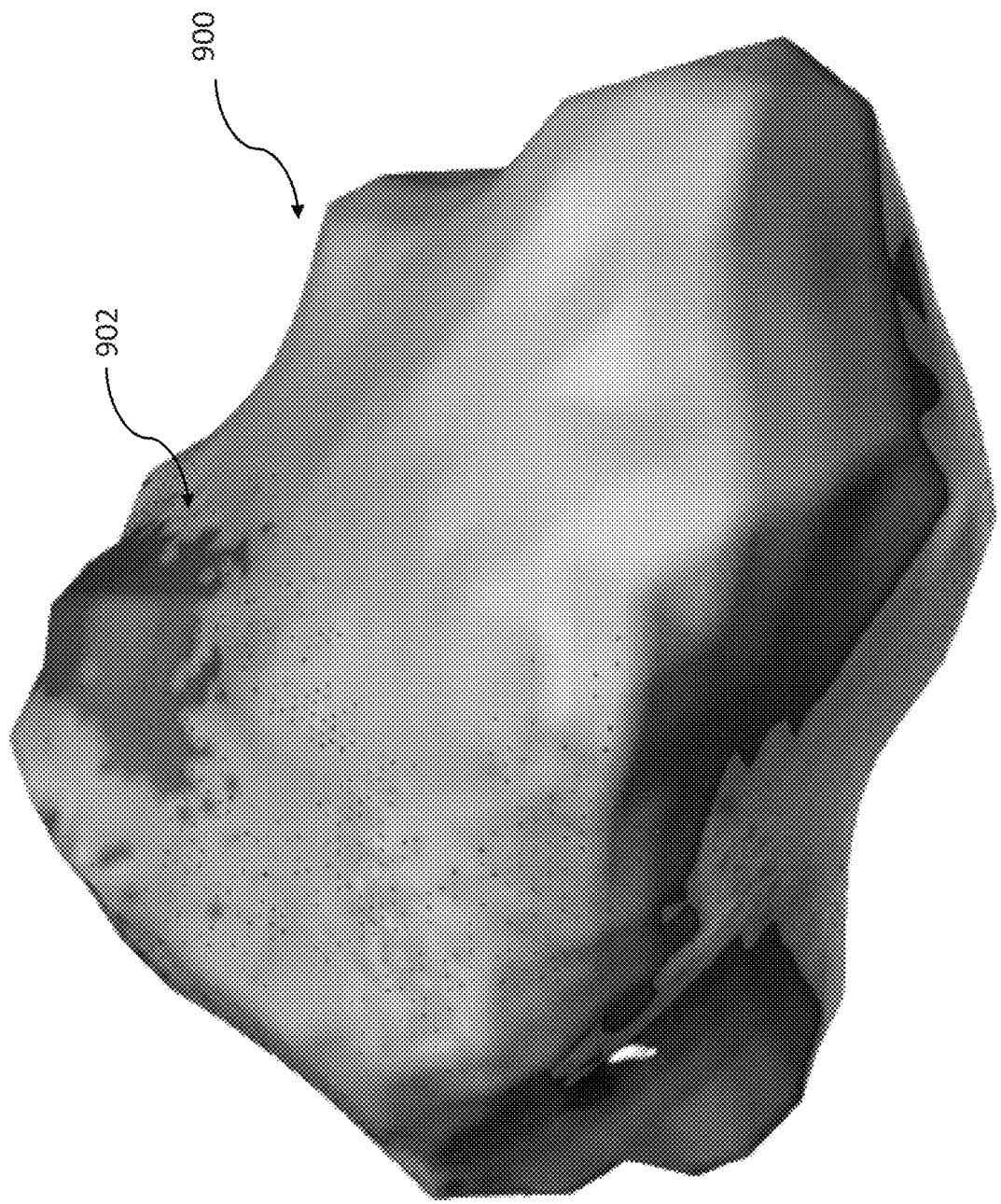
Figure 10:
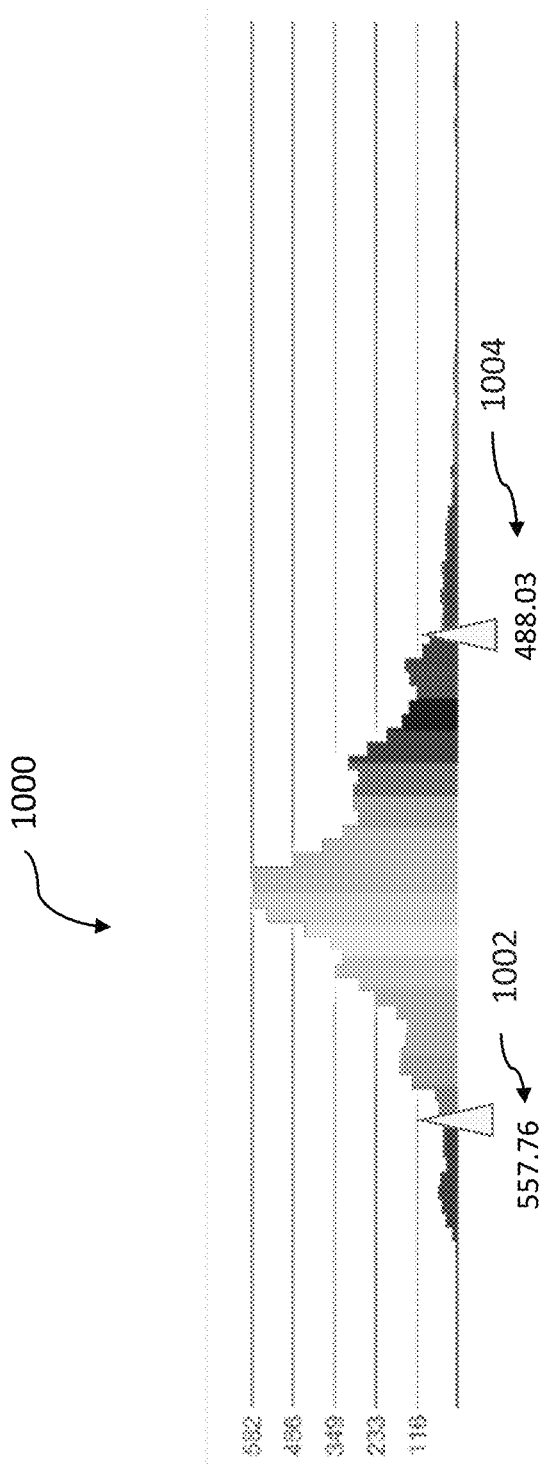

To improve things a little, considered the histogram 800 (FIG. 8). Here, a left control numeral 802 is moved to the right to the value by 557.76 which is a value corresponding to which the number of data points in the histogram is starting to increase. This indicates that there is underlying data for values below 557.76. When the left control is moved to the value numeral 557.76 as described, the cardiac map is dynamically re-colored to produce the map 900 (FIG. 9). Immediately one can see that the map has less green and more of the color is being assigned to areas for which there is underlying data. Thus, the resolution of the map is improving, and the electrophysiologist can tell more about state of the underlying tissue. For example, there is a distinct region 902 colored red now starting to form.

Figure 11:
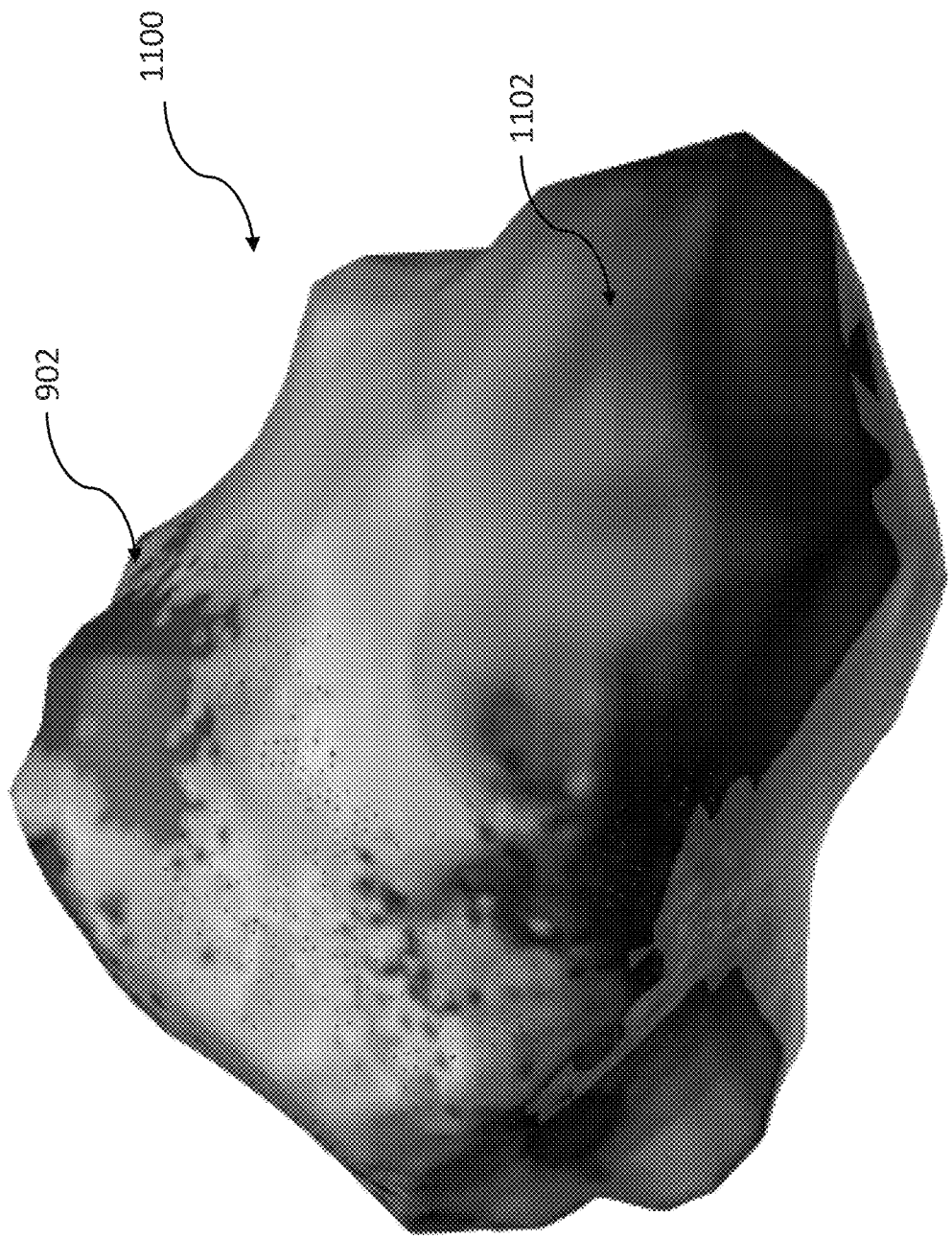
Figure 12:
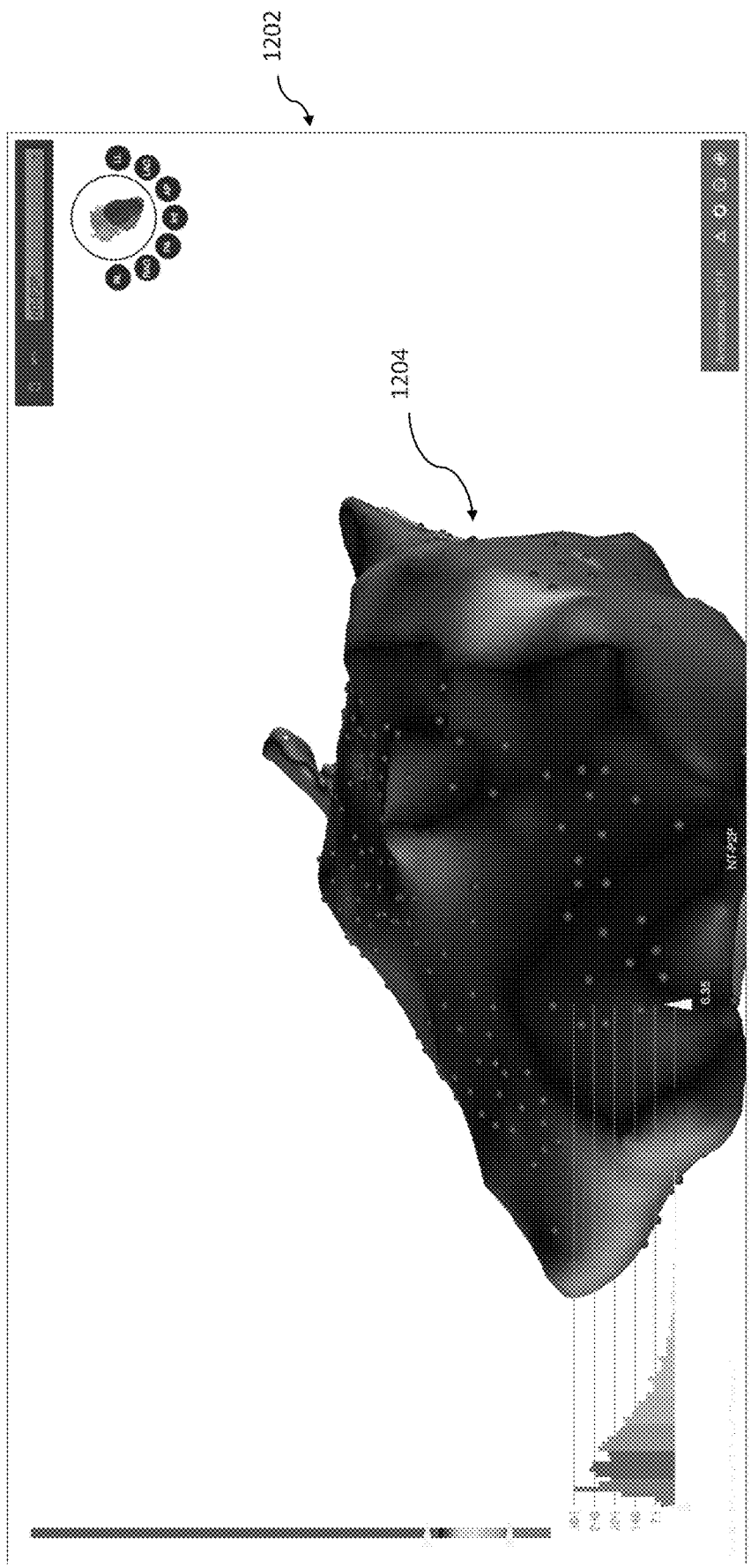
FIG. 12 illustrates a graphical user interface in a first state, in accordance with an embodiment of the invention.

FIG. 12 shows a histogram 1000, which is a progression from the histogram 900 and with the difference being that the right caliper or control has been moved to the left to the value of 488.03, to coincide with the portion of the histogram where to the left of said value there is an increase in the data. As a result, the histogram 1000 produces a change in the color scale of the cardiac map, as is shown in the map 1100 (FIG. 11). As will be seen, the map 1100 includes the red region 902 already described, but said map now additionally includes a deep blue region indicated by reference numeral 1102 which was not previously seen.

Thus, it will be appreciated that by interactively adjusting the position of the controls in the histogram, the color scale used to color the cardiac map may be adjusted so that the application of color can be limited to a data range for which meaningful data has been collected. Stated another way, the histogram by showing the number of data points collected for each value of the metric, provides an operator/electrophysiologist with a visualization of where the data actually resides so that the color scale can be dynamically adjusted to fit the actual data, thereby showing more information that is useful.

Referring again to FIG. 6 of the drawings, responsive to the adjustment of the left and right controls of the histogram, at block numeral 602 the cardiac map is colored according to a color scale indicated by user-positioning of the histogram controls, as described.

In one embodiment, the map generator 134 is provisioned to generate a graphical user interface (GUI) numeral 1200, shown in FIG. 12 of the drawings, as will now be described. As will be seen, the GUI numeral 1200 includes a first portion indicated by reference numeral 1202, within which is displayed an electro-anatomical map 1204 of a heart. The map 1204 is advantageously produced in accordance with the techniques described above and is colored in accordance with a color-scale to indicate values associated with an underlying metric, for example activation times, currently being depicted on the map. Thus, the map 1204 is based on a plurality of measurement points within the heart for which data was collected, in accordance with the techniques described above.

Figure 13:
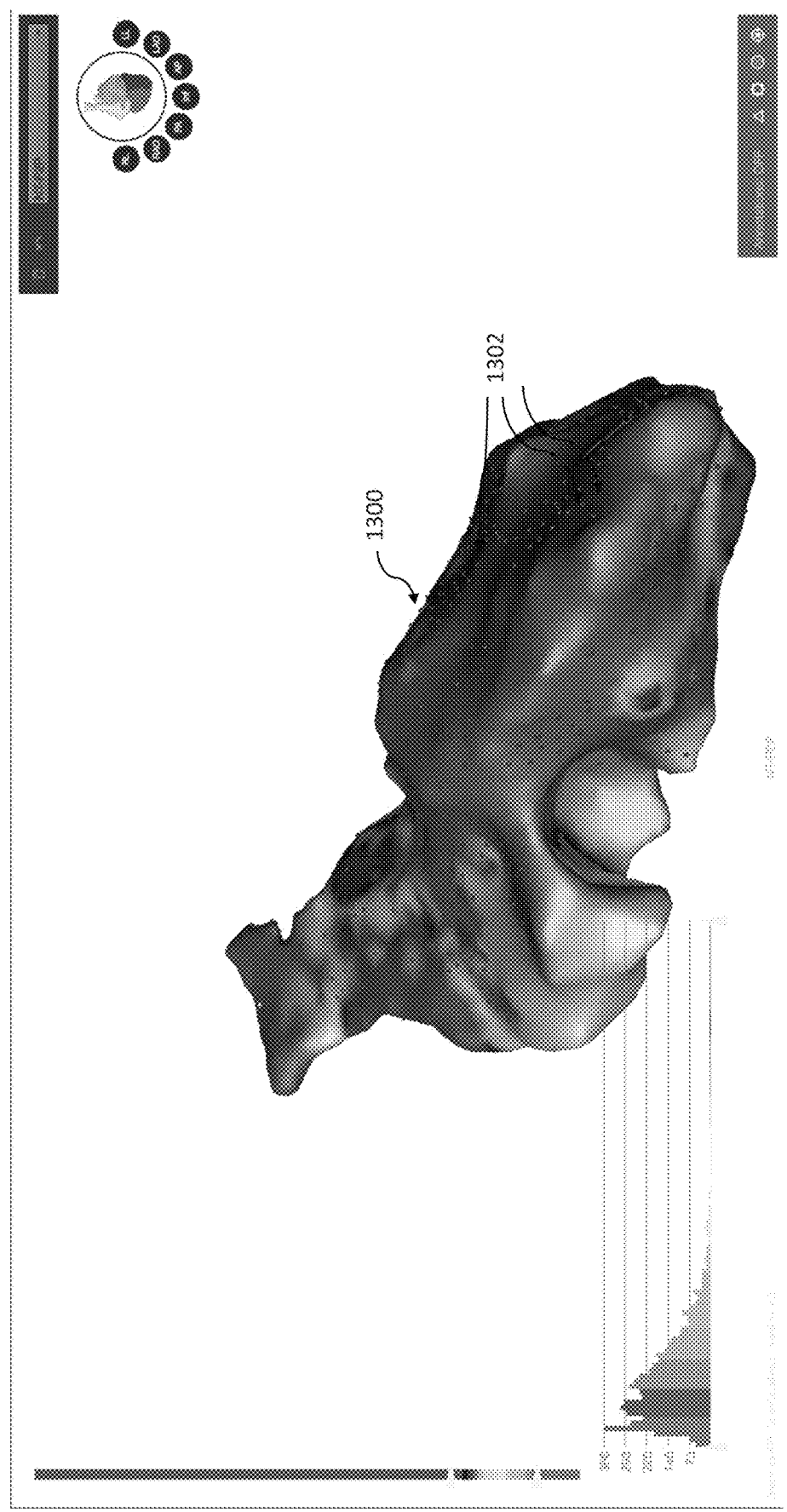
FIG. 13 illustrates a portion of graphical user interface of FIG. 12 in another large-scale, in accordance with an embodiment of the invention.

Referring now to FIG. 13 of the drawings, reference numeral 1300 indicates the map of FIG. 12, shown in an expanded scale so that the plurality of measurement points/locations within the heart can be seen—each measurement point is indicated by a marker in the form of a dot indicated by reference numeral 1302. Each of the measurement points/locations 1302 is displayed spatially in relation to the geometry of the heart. Moreover, the GUI is configured so that each of the measurement points/locations 1302 is user-selectable. For example, in use, a user, such as an electrophysiologist, may operate a pointing device such as a mouse to select one of the measurement points/locations 1302. Responsive to said selection of a measurement point/locations 1302, in one embodiment, the mapping system 112 retrieves the data associated with the selected measurement point/location 1302. For example, the data may include any metric computed and associated with the selected point/location, and/or actual measurement values collected for the location 1302. In one embodiment, the GUI 1200 is configured to display in a second portion 1400 (see FIG. 14), the metrics/measurement values associated with the selected location 1302.

Disclosed above is a technique for coloring an electro-anatomical map in accordance with a color scale selected to indicate the condition of underlying cardiac tissue. Adding to the usefulness of said technique to color the electro-anatomical map, a further embodiment of the present invention allows for a user to toggle the map between a first state in which the coloration of the map may be viewed, and a second state in which the underlying metrics/data is associated with a particular point in the map may be viewed. This allows an electrophysiologist/clinician the ability to perform deeper analysis given that the underlying metrics associated with particular points on a cardiac map can now also be analyzed, in real-time.

Figure 14:
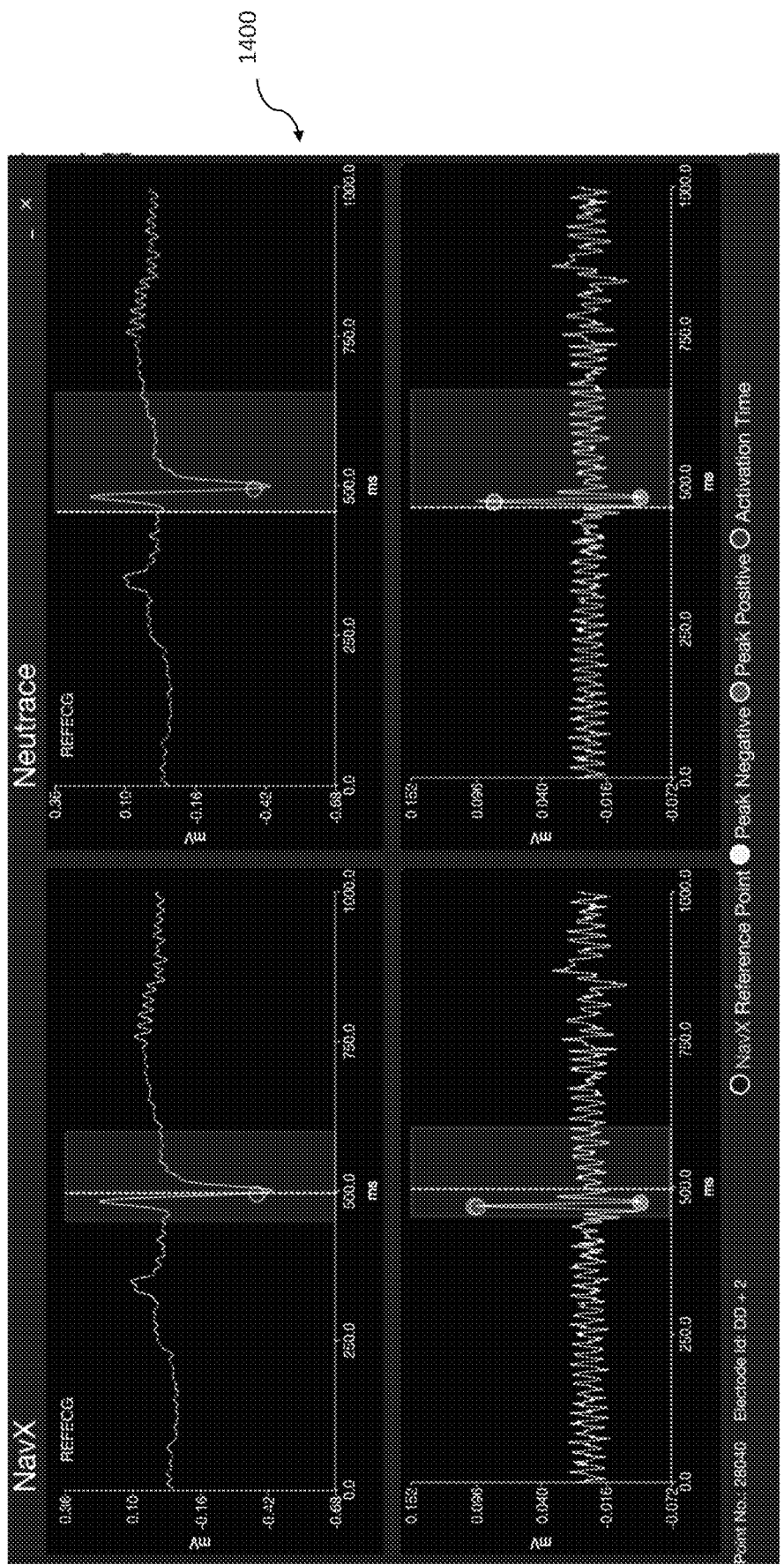
FIG. 14 illustrates the graphical user interface in a second state, in accordance with an embodiment of the invention.
Figure 15:
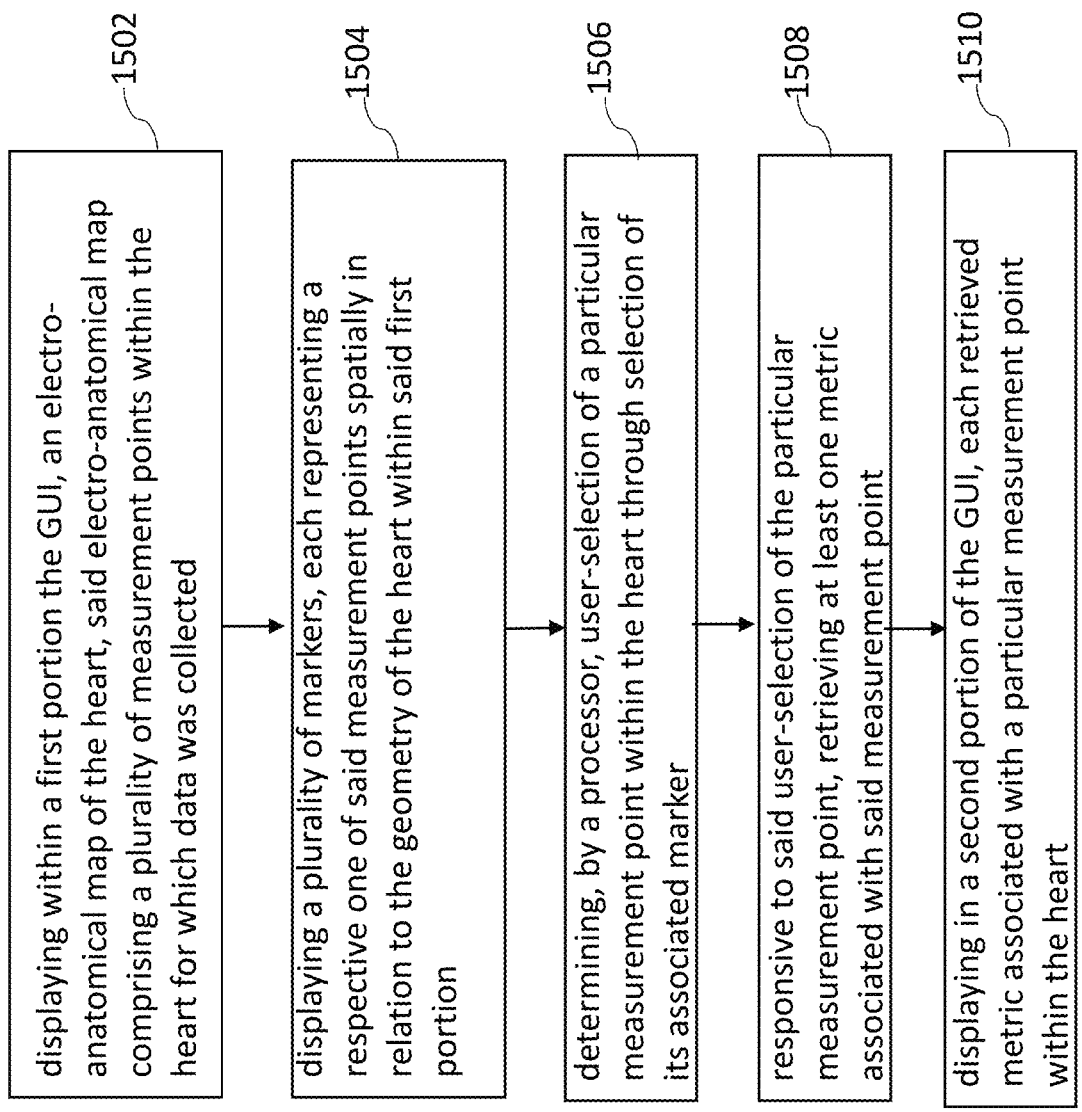
FIG. 15 a flowchart of operations to toggle the graphical interface between the two states, in accordance with an embodiment of the invention.

The ability to toggle the map has been described with reference to FIGS. 12-14 above. Further, FIG. 15 outlines the steps that a graphical user interface performs in order to toggle the map as described.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 16.

Figure 16:
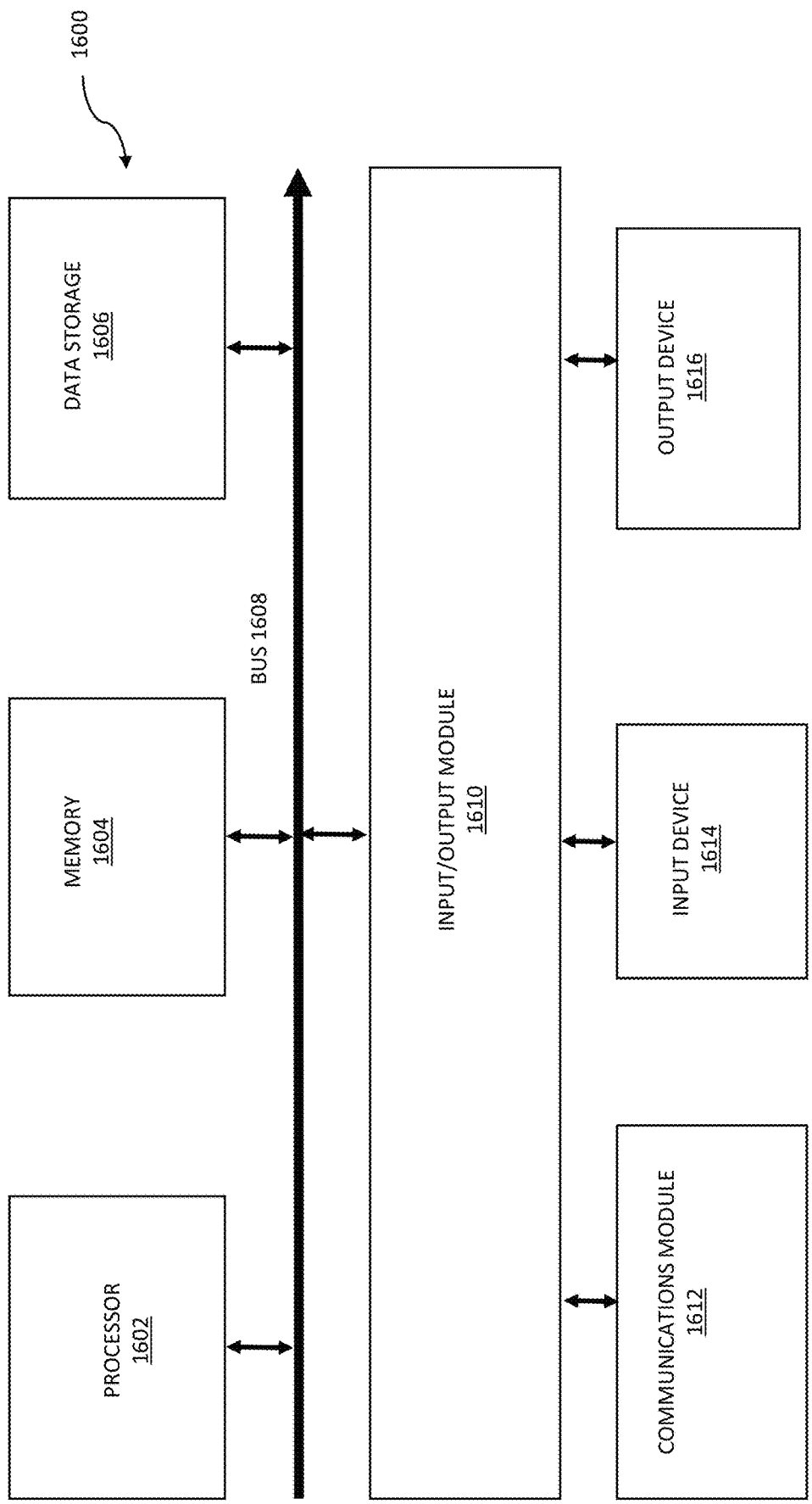
FIG. 16 shows a high-level block diagram of hardware for implementing the exemplary diagnostic/treatment system, in accordance with an embodiment of the invention.

FIG. 16 is a block diagram illustrating exemplary hardware for executing some of the techniques disclosed herein, in accordance with one embodiment of the invention. In certain aspects, the computer system 1600 may be implemented using hardware or a combination of software and hardware, either in a dedicated server or integrated into another entity or distributed across multiple entities.

Computer system 1600 (e.g., client or server) includes a bus 1608 or other communication mechanism for communicating information, and a processor 1602 coupled with bus 1608 for processing information. According to one aspect, the computer system 1600 may be implemented as one or more special-purpose computing devices. The special-purpose computing device may be hard-wired to perform the disclosed techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques. By way of example, the computer system 1600 may be implemented with one or more processors 1602. Processor 1602 may be a general-purpose microprocessor, a microcontroller, a Digital Signal Processor (DSP), an ASIC, a FPGA, a Programmable Logic Device (PLD), a controller, a state machine, gated logic, discrete hardware components, or any other suitable entity that can perform calculations or other manipulations of information.

Computer system 1600 can include, in addition to hardware, code that creates an execution environment for the computer program in question, e.g., code that constitutes processor firmware, a protocol stack, a database management system, an operating system, or a combination of one or more of them stored in an included memory 1604 such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 1608 for storing information and instructions to be executed by processor 1602. The processor 1602 and the memory 1604 can be supplemented by, or incorporated in, special purpose logic circuitry. Expansion memory may also be provided and connected to computer system 1600 through input/output module 1610, which may include, for example, a SIMM (Single in Line Memory Module) card interface Such expansion memory may provide extra storage space for computer system 1600 or may also store applications or other information for computer system 1600. Specifically, expansion memory may include instructions to carry out or supplement the processes described above and may include secure information also. Thus, for example, expansion memory may be provided as a security module for computer system 1600 and may be programmed with instructions that permit secure use of computer system 1600. In addition, secure applications may be provided via the SIMM cards, along with additional information, such as placing identifying information on the SIMM card in a non-hackable manner.

The instructions may be stored in the memory 1604 and implemented in one or more computer program products, i.e., one or more modules of computer program instructions encoded on a computer readable medium for execution by, or to control the operation of, the computer system 1600, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, embeddable languages, and xml-based languages. Memory 1604 may also be used for storing temporary variable or other intermediate information during execution of instructions to be executed by processor 1602.

A computer program as discussed herein does not necessarily correspond to a file in a file system. A program can be stored in a portion of a tile that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 1670 further includes a data storage device 1606 such as a magnetic disk or optical disk, coupled to bus 1608 for storing information and instructions. Computer system 1600 may be coupled via input/output module 1610 to various devices. The input/output module 1610 can be any input/output module. Example input/output modules 1610 include data ports such as USB ports. In addition, input/output module 1610 may be provided in communication with processor 1602, so as to enable near area communication of computer system 1600 with other devices. The input/output module 1610 may provide, for example, for wired communication in some implementations, or for wireless communication in other implementations, and multiple interfaces may also be used. The input/output module 1610 is configured to connect to a communications module 1612. Example communications modules 1612 include networking interface cards, such as Ethernet cards and modems.

The components of the system can be interconnected by any form or medium of digital data communication, e.g., a communication network. The communication network can include, for example, any one or more of a PAN, a LAN, a CAN, a MAN, a WAN, a BBN, the Internet, and the like. Further, the communication network can include, but is not limited to, for example, any one or more of the following network topologies, including a bus network, a star network, a ring network, a mesh network, a star-bus network, tree or hierarchical network, or the like.

For example, in certain aspects, communications module 1612 can provide a two-way data communication coupling to a network link that is connected to a local network. Wireless links and wireless communication may also be implemented. Wireless communication may be provided under various modes or protocols, such as GSM (Global System for Mobile Communications), Short Message Service (SMS), Enhanced Messaging Service (EMS), or Multimedia Messaging Service (MMS) messaging, CDMA (Code Division Multiple Access), Time division multiple access (TDMA), Personal Digital Cellular (PDC), Wideband CDMA, General Packet Radio Service (GPRS), or LTE (Long-Term Evolution), among others. Such communication may occur, for example, through a radio-frequency transceiver. In addition, short-range communication may occur, such as using a BLUETOOTH, WI-FI, or other such transceiver.

In any such implementation, communications module 1612 sends and receives electrical, electromagnetic or optical signals that carry digital data streams representing various types of information. The network link typically provides data communication through one or more networks to other data devices. For example, the network link of the communications module 1612 may provide a connection through local network to a host computer or to data equipment operated by an Internet Service Provider (ISP). The ISP in turn provides data communication services through the world-wide packet data communication network now commonly referred to as the Internet. The local network and Internet both use electrical, electromagnetic or optical signals that carry digital data streams. The signals through the various networks and the signals on the network link and through communications module 1612, which carry the digital data to and from computer system 1600, are example forms of transmission media.

Computer system 1600 can send messages and receive data, including program code, through the network(s), the network link and communications module 1612. In the Internet example, a server might transmit a requested code for an application program through Internet, the ISP, the local network and communications module 1610. The received code may be executed by processor 1602 as it is received, and/or stored in data storage 1606 for later execution.

In certain aspects, the input/output module 1610 is configured to connect to a plurality of devices, such as an input device 1612 (e.g., input device 1614) and/or an output device 1614 (e.g., output device 1614). Example input devices 1612 include a stylus, a finger, a keyboard and a pointing device, e.g, a mouse or a trackball, by which a user can provide input to the computer system 1600. Other kinds of input devices 1612 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 1614 include display devices, such as a LED (light emitting diode), CRT (cathode ray tube), LCD (liquid crystal display) screen, a TFT LCD (Thin-Film-Transistor Liquid Crystal Display) or an OLED (Organic Light Emitting Diode) display, for displaying information to the user. The output device 1614 may comprise appropriate circuitry for driving the output device 1614 to present graphical and other information to a user.

According to one aspect of the present disclosure, the techniques disclosed herein may be implemented on the computer system 1600 in response to processor 1602 executing one or more sequences of one or more instructions contained in memory 1604. Such instructions may be read into memory 1604 from another machine-readable medium, such as data storage device 1606. Execution of the sequences of instructions contained in main memory 1604 causes processor 1602 to perform the process steps described herein. One or more processors in a multi-processing arrangement may also be employed to execute the sequences of instructions contained in memory 1604. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g, a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components.

Computing system 1600 can include clients and servers. A client and server are generally remote from each other and typically interact through a communication network. The relationship of client and server arises by virtue of computer programs running on the respective computers and having a client-server relationship to each other. Computer system 1600 can be, for example, and without limitation, a desktop computer, laptop computer, or tablet computer. Computer system 1600 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer-readable medium" as used herein refers to any medium or media that participates in providing instructions or data to processor 1602 for execution. The term "storage medium" as used herein refers to any non-transitory media that store data and/or instructions that cause a machine to operate in a specific fashion. Such a medium may take many forms, including, but not limited to, non-volatile media, volatile media, and transmission media. Non-volatile media include, for example, optical disks, magnetic disks, or flash memory, such as data storage device 1606. Volatile media include dynamic memory, such as memory 1604. Transmission media include coaxial cables, copper wire, and fiber optics, including the wires that comprise bus 1608. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

As used in this specification of this application, the terms "computer-readable storage medium" and "computer-readable media" are entirely restricted to tangible, physical objects that store information in a form that is readable by a computer. These terms exclude any wireless signals, wired download signals, and any other ephemeral signals. Storage media is distinct from but may be used in conjunction with transmission media. Transmission media participates in transferring information between storage media. For example, transmission media includes coaxial cables, copper wire and fiber optics, including the wires that comprise bus 1608. Transmission media can also take the form of acoustic or light waves, such as those generated during radio-wave and infra-red data communications. Furthermore, as used in this specification of this application, the terms "computer", "server", "processor", and "memory" all refer to electronic or other technological devices. These terms exclude people or groups of people. For the purposes of the specification, the terms display or displaying means displaying on an electronic device.

To illustrate the interchangeability of hardware and software, items such as the various illustrative blocks, modules, components, methods, operations, instructions, and algorithms have been described generally in terms of their functionality. Whether such functionality is implemented as hardware, software or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A. B, or C" each refer to only A, only B, or only C; any combination of A, B, and C; and/or at least one of each of A, B, and C.

To the extent that the term "include," "have," or the like is used in the description or the claims, such term is intended to be inclusive in a manner similar to the term "comprise" as "comprise" is interpreted when employed as a transitional word in a claim. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way

The invention claimed is:

1. A method for a graphical user-interface (GUI) of a computer system, the method comprising:
    displaying within a first portion of the GUI, an electro-anatomical map of a heart, said electro-anatomical map comprising a plurality of measurement points;
    displaying a plurality of markers, wherein each marker of the plurality of markers representing a respective measurement point of the plurality of measurement points, and wherein the plurality of markers is displayed spatially in relation to a geometry of the heart within said first portion;
    receiving, by a processor, user-selection of a particular measurement point through selection of the associated marker from the first portion of the GUI;
    responsive to said user-selection of the particular measurement point from the first portion of the GUI, retrieving at least one metric associated with said particular measurement point;
    displaying in a second portion of the GUI, each retrieved metric associated with said particular measurement point;
    receiving user-selection of a color scale associated with a data range shown on the electro-anatomical map, wherein the data range indicates a range of a number of measurement points in the plurality of measurement points for each of the at least one metric;
    coloring the electro-anatomical map based on said color scale associated with said data range shown on the electro-anatomical map; and
    providing a control mechanism to allow a user to dynamically adjust said color scale, wherein said control mechanism comprises an interactive histogram, with adjustable controls that can be moved to select the data range to be colored, and wherein the color scale is dynamically adjusted to match the data range.

2. A system comprising:
    a map generator component to generate mapping data associated with an electro-anatomical map of a heart, wherein the map generator component is configured to generate a graphical user interface (GUI);
    a display, connected to the map generator component, to render the graphical user interface comprising a first portion within which the electro-anatomical map of the heart is displayed, said electro-anatomical map comprising a plurality of measurement points, including the displaying of a plurality of markers, wherein each marker of the plurality of markers is representing a respective measurement point of the plurality of measurement points, and wherein the plurality of markers is displayed spatially in relation to a geometry of the heart within said first portion;

a processor configured to:
 receive user-selection of a particular measurement point through selection of the associated marker from the first portion of the GUI,
  wherein the graphical user interface is configured to, in response to said user-selection of the particular measurement point from the first portion of the GUI, retrieve at least one metric associated with said particular measurement point;
 control the display to display in a second portion of the GUI, each retrieved metric associated with said particular measurement point;
 receive user-selection of a color scale associated with a data range shown on the electro-anatomical map, wherein the data range indicates a range of a number of measurement points in the plurality of measurement points for each of the at least one metric; and
 color the electro-anatomical map based on said color scale associated with said data range shown on the electro-anatomical map; and
a control mechanism to allow a user to dynamically adjust said color scale, wherein said control mechanism comprises an interactive histogram, with adjustable controls that can be moved to select the data range to be colored, and wherein the color scale is dynamically adjusted to match the data range.

3. A non-transitory computer readable storage medium, having stored thereon, a set of computer-executable instructions that causes a computer to perform a method for a graphical user interface (GUI), comprising:
 displaying within a first portion of the GUI, an electro-anatomical map of a heart, said electro-anatomical map comprising a plurality of measurement points;
 displaying a plurality of markers, wherein each marker of the plurality of markers representing a respective measurement point of the plurality of measurement points, and wherein the plurality of markers is displayed spatially in relation to a geometry of the heart within said first portion;
 receiving, by a processor, user-selection of a particular measurement point within the heart through selection of the associated marker from the first portion of the GUI;
 responsive to said user-selection of the particular measurement point from the first portion of the GUI, retrieving at least one metric associated with said particular measurement point;
 displaying in a second portion of the GUI, each retrieved metric associated with said particular measurement point;
 receiving user-selection of a color scale associated with a data range shown on the electro-anatomical map, wherein the data range indicates a range of a number of measurement points in the plurality of measurement points for each of the at least one metric;
 coloring the electro-anatomical map based on said color scale associated with said data range shown on the electro-anatomical map; and
 providing a control mechanism to allow a user to dynamically adjust said color scale, wherein said control mechanism comprises an interactive histogram, with adjustable controls that can be moved to select the data range to be colored, and wherein the color scale is dynamically adjusted to match the data range.

\* \* \* \* \*